United States Patent [19]

Sallay

[11] Patent Number: 4,493,898
[45] Date of Patent: Jan. 15, 1985

[54] METHOD FOR DETECTING AND MONITORING CANCER

[75] Inventor: Stephen I. Sallay, Fort Wayne, Ind.

[73] Assignee: Purdue Research Foundation, West Lafayette, Ind.

[21] Appl. No.: 488,133

[22] Filed: Apr. 25, 1983

[51] Int. Cl.³ .................... G01N 31/02; G01N 33/48; G01N 33/68
[52] U.S. Cl. ...................... 436/64; 436/87; 436/175; 436/177
[58] Field of Search ....................... 436/64, 71, 86, 87, 436/88, 175, 177, 813, 164

[56] References Cited

U.S. PATENT DOCUMENTS

| | | | |
|---|---|---|---|
| 4,115,062 | 9/1978 | Morre et al. | 436/71 X |
| 4,146,603 | 3/1979 | Davidson et al. | 436/540 X |
| 4,171,204 | 10/1979 | Schwenzer et al. | 436/175 |
| 4,180,556 | 12/1979 | Kim et al. | 436/813 X |

OTHER PUBLICATIONS

Warren, J. of Biological Chemistry, vol. 234, No. 8, pp. 1971–1975, (Aug. 1959).

Primary Examiner—Arnold Turk
Assistant Examiner—Robert J. Hill, Jr.
Attorney, Agent, or Firm—Bacon & Thomas

[57] ABSTRACT

A method for diagnosing and monitoring cancer, which comprises precipitating certain components from blood serum by addition of a benzenesulfonic acid or a benzylsulfonic acid, determining the sialic acid content of the supernatant, and comparing its sialic acid content with the sialic acid content of sera from healthy subjects after identical treatment. The determination of the sialic acid by the thiobarbituric acid colorimetric method is improved by addition of N,N-dimethylacetamide during development of the chromophore.

10 Claims, No Drawings

METHOD FOR DETECTING AND MONITORING CANCER

The present invention relates to the diagnosis and the clinical monitoring of tumor patients. More particularly, it relates to the detection of malignancy and to following the effectiveness of radiation therapy and/or chemotherapy.

Tumor cells exhibit many abnormalities relating to the biochemical composition of their cell membranes. During the past decade, it became increasingly evident that some of these molecular changes are essential in the process of malignant transformations of cells. Among these cell surface membrane molecular abnormalities, the change in sialic acid level is noteworthy. Sialic acid "SA" (N-acetylneuraminic acid) is one of the sugar components of cell membranes and is a member of the generic class of acylated neuraminic acids. They are chemically well-defined and recognized as building blocks of glycoproteins, glycolipids, oligosaccharides, and polysaccharides, and only very small quantities are found in the free state.

The central role of SA in cell adhesion, cell surface change, and cell survival is well established (e.g., J. R. Durocher et al., Blood, 45, 11-20, 1975; C. W. Lloyd, Biophys. Acta, 458, 1-71, 1976). It has also been shown that some of these SA-containing cell membrane biomolecules are involved in cellular recognition, cell-cell interactions, and as causal agents in tumorigenesis (e.g., S. I. Hakomori et al, Proc. Natl. Acad. Sci., USA, 59, 254-261, 1968; S. Roseman, Chem. Phys. Lipids, 5, 270-297, 1970; S. I. Hakomori, Advances in Cancer Research, G. Klein and S. Weinhouse (eds.), Academic Press, New York, N.Y., Vol. 18, pp. 265-315, 1974). Recently, it was found that cell surface SA is positively correlated with the metastatic potential of tumor cells (G. Yogeeswaran et al., Science, 212, 1514-1516, 1981).

It is a generally accepted view that about 80% of the sugar molecules, such as SA, are located on the outer surface of cell membranes. Furthermore, it is believed that one of the roles of these sugar residues is to secure and protect the biological functions of the membrane proteins against hostile environments. During tumorigenesis along with other sugar molecules, SA residues are added enzymatically onto the surface of the malignant cell membranes.

Indeed, it has been established earlier that the SA-containing cell membrane components, which are shed into the blood stream, show significant SA elevation in tumor sera in comparison with healthy sera (e.g., A. Rosenberg et al., in Biological Roles of Sialic Acid, A. Rosenberg and C-L. Schengrund (eds.), Plenum Press, N.Y. and London, pp. 275-294, 1976).

In light of the above, it is not surprising that SA has undergone extensive research in recent years to further elucidate its biological function and to explore its potential as a biological marker for cancer diagnosis and for clinical monitoring of malignancies.

During the past decade, numerous research groups reported elevated SA levels in tumor sera (e.g., A. M. Dnistrian et al., Cancer, 50, 1815-1819, 1982 and references therein). Recently, a reexamination of some of these techniques were carried out on the same set of sera in my laboratory (S. I. Sallay et al., Proc. 13th International Cancer Congress, Seattle, p. 346, 1982). Thus, the total serum SA levels (e.g., H. K. B. Silver et al., J. Chrom., 224 (1981) 381-388 and references therein), the SA values of the ganglioside-bound sera fractions (T. M. Kloppel et al., Proc. Natl. Acad. Sci., USA, 74, 3011-3013, 1977; J. D. Morré et al., U.S. Pat. No. 4,115,062, 1978) and the SA levels of the perchloric acid (PCA) soluble sera fractions (A. Lipton et al., Cancer, 43, 1766-1771, 1979; E. A. Davidson et al., U.S. Pat. No. 4,146,603, 1979; and H. A. Harvey et al., Cancer, 47, 324-327, 1981) were compared. Among these approaches, the PCA soluble sera fraction secured the highest cancer/normal SA level ratios.

Earlier, Winzler et al. (J. Clin. Investigation, 27, 609-616 and 617-619, 1948) partially precipitated proteins from plasma with PCA, trichloroacetic acid or sulfosalicyclic acid, but they selected 0.6 M PCA as the standard means for making this separation, and found that the supernatant contained a small amount of nondialyzable "mucoproteins" (sialoglycoproteins). They also observed that these PCA soluble tumor-associated mucoproteins have an acidic character with an isoelectric point of pH 4.5.

In 1955, Winzler reported significant elevations of protein-bound SA in patients with cancer, using the PCA supernatant for SA determination (R. J. Winzler, in Methods of Biochemical Analysis, D. Glick (ed.), Interscience Publishers, Inc., N.Y., Interscience Publishers Ltd., London, Vol. II, pp. 279-311, 1955).

Over two decades later, Lipton et al. (Cancer 43, 1766-1771, 1979); Harvey et al. (Cancer, 47, 324-327, 1981); and Davidson et al. (U.S. Pat. No. 4,146,603, filed Feb. 18, 1977, issued Mar. 27, 1979), using the technology of Winzler et al. (vide supra), showed the usefulness of the SA levels of the PCA soluble serum fraction for determining or monitoring malignancy. Applying Winzler's method, these workers also used 0.6 M perchloric acid for selective protein precipitation, and found that the PCA soluble proteins showed a similar isoelectric point of 4.2-4.6.

The perchloric acid method was subsequently simplified and improved in my laboratory by directly using PCA and after precipitation diluting the supernatant to 0.1 N, for the hydrolysis of the SA residues.

It was, however, found that using Warren's colorimetric SA determination technique (L. Warren, J. Biol. Chem., 234, 1971-1975, 1959), the molecular absorption coefficients of SA in the presence of 0.1 N PCA differ ($\epsilon_{549}=57,000$, $\epsilon_{532}=22,000$) from the molecular absorption observed in water or in 0.1 N sulfuric acid which I established in my laboratory ($\epsilon_{549}=64,000$, $\epsilon_{532}=24,000$). The molecular absorption values for the colorimetrically interfering deoxyribase were practically identical both in water 0.1 N sulfuric acid N in 0.1 N PCA ($\epsilon_{549}^{water}=52,000$, $\epsilon_{549}^{PCA}=54,000$ and $\epsilon_{532}^{water}=177,000$, $\epsilon_{532}^{water}=174,000$). Using the relevant absorption values, identical SA levels were obtained in water, 0.1 N sulfuric acid or in 0.1 N PCA solutions.

The above simplification of technology saved three steps: (a) KOH neutralization of PCA; (b) centrifugation of the $KClO_4$ precipitate; and (c) the readjustment of acidity to 0.1 N sulfuric acid applied by the Davidson patent (loc. cit.).

I have now discovered a new method and means for separating a richer population of tumor-associated proteins from blood serum and after a mild acidolysis measuring the SA content thereof.

An object of my invention is to provide a screening test for malignancy.

Another object is to provide a method for monitoring the progress of a cancer patient during and following chemotherapy and/or radiation therapy.

A further object is to provide guidance to the physician for the early recognition of malignancy or the recurrence of active tumor burden in patients previously in remission.

Another object of this invention is to secure an inexpensive, simple, rapid, highly reproducible tumor-monitoring technology which can be readily automated in clinical laboratories.

Other objects will be apparent from the following description.

I have discovered that benzenesulfonic acid and the lower-alkylbenzenesulfonic acids or benzylsulfonic acid and lower alkylbenzylsulfonic acids are superior agents for selectively precipitating proteins from blood serum, thus enriching the supernatant in tumor-associated glycoproteins which are markers for malignancy. Preferable are the lower-alkylbenzenesulfonic acids, in particular p-toluenesulfonic acid (TSA).

According to Davidson et al. (vide supra), molecular weights of the PCA supernatant glycoproteins range between 50,000 to 70,000 Daltons. Polyacrylamide-gel electrophoresis (SDS-PAGE) of my TSA supernatants detected proteins with apparent molecular weights of about 11,200, 23,400–25,400, 43,600–46,500, 58,800 and 69,600–70,800 Daltons. Furthermore, gel-electrophoresis showed significantly more proteins in the TSA supernatants than in the PCA fractions. Also, the electrophoretic mobilities of the TSA supernatant proteins differed from the PCA supernatants when the experiments were carried out on the same set of healthy and tumor sera.

Further studies of the TSA supernatants included the total amino acid analysis of three healthy and three tumor sera. As a result, marked differences were found between the TSA and PCA supernatants in both healthy and tumor sera series.

One of the conspicuous differences in the amino acid composition of the TSA and PCA supernatants was shown by their methionine and tyrosine content. Whereas, healthy TSA supernatants have shown a 20.29±2.39 microgram (mcg)/ml serum methionine and 113.8±22.5 mcg/ml serum tyrosine content, the proteins of the corresponding PCA supernatants did not contain any of these essential amino acids. Furthermore, whereas the tumor TSA supernatants contained 37.6±6.57 mcg/ml serum methionine and 234.82±19.57 mcg/ml serum tyrosine, the corresponding PCA supernatants showed no methionine and only a trace amount (6.52±11.6 mcg/ml serum) of tyrosine.

The net negative charge of the TSA supernatants from healthy volunteers was 16% higher than the corresponding values for the PCA supernatants. In the TSA and PCA preparations of the tumor patients, this difference was only 1%.

Furthermore, the amount of basic amino acids of the TSA supernatants of healthy volunteers was 23% higher than that of the corresponding PCA fractions. Finally, the amount of basic amino acids in the TSA supernatants of the tumor patients was 13% higher than in their PCA fractions.

Furthermore, whereas a mean value of 65±10 mcg/ml SA for healthy sera of the PCA soluble fraction was found by Lipton et al. (loc. cit.), the newly developed TSA method showed an 85±16 mcg/ml SA average value. This finding indicates an average of 30% higher 0.1 N acid hydrolyzable SA content in the TSA supernatant than in the PCA fraction.

Finally, Lipton et al. have found an average value of 130±40 mcg/ml SA in the active tumor sera PCA soluble fraction. The TSA method showed a 177 mcg/ml SA mean value. Thus, the new TSA soluble fraction exhibited an average of 36% higher SA content than that of the PCA technique.

The above-presented study clearly demonstrates the significant differences between the protein content of the TSA and PCA supernatants.

In one embodiment of the invention, I commingle blood serum with an equal volume of aqueous 1.0 M p-toluenesulfonic acid. The resulting solids (largely acid-insoluble proteins and glycolipids) are separated by centrifugation. The supernatant is diluted with water to 0.1 N p-toluenesulfonic acid, and is heated at 80° C. for one hour. Free SA is released thereby in the liquid phase, and is determined in a conventional manner, such as by reaction with thiobarbituric acid and measurement of the resulting red chromophore with a UV-spectrophotometer, according to the method of Warren (vide supra). The results are expressed in terms of micrograms of sialic acid per milliliter (mcg/ml) of the original serum.

While the above procedure and conditions are preferred, and while it goes without saying that, for analytical/diagnostic results to be comparable they should be obtained under a standard set of controlled conditions, it will nevertheless be apparent that my new diagnostic procedure can be operated successfully under conditions differing from those set forth above, provided a sufficient number of serum samples are analyzed to establish the dividing line in sialic acid content between cancer and healthy sera.

The benzenesulfonic acid or benzylsulfonic acid can be unsubstituted or substituted with methyl, ethyl, n-propyl, or isopropyl in the ortho, meta, or para position. The concentration of the acid stock solution can range from about 0.2 to 2.0 molar, and the ratio of acid to serum can range inversely from around 2:1 to around 1:2.

The effect of the final acid concentration of the reaction mixture was studied by adjusting its molarity between 0.1 to 1.0 by adding the acid stock solution (0.2–2.0 M) and the required amount of water to the serum. The results on a set of tumor and healthy sera showed that the best cancer/normal SA ratios were obtained by rendering the final acidity to 0.5 M. Below or above 0.5 M acidity, the cancer/normal sera SA ratios rapidly decreased.

p-Toluenesulfonic acid was proven to be a mild reagent. After 1 hour/80° C. heating of SA stock solution in 0.1 M TSA, 96% of the SA was recovered (measured by the Warren procedure, loc. cit.). The reproducibility of the TSA method on five samples and different days showed a ±2% of SD. The overall SD, estimated on fifty duplicates, was +4 μg SA/ml serum.

It was also found that the thiobarbituric acid (TBA) colorimetric assay of Warren (loc. cit.) provided better SA level ratios between the tumor/normal TSA supernatants than the resorcinol test (L. Svennerholm, Biochim. Biophys. Acta, 24, 604–611, 1957 and S. I. Sallay et al., vide supra).

The protein-bound SA hydrolysis of the TSA supernatants is preferably carried out with the acid concentration diluted to around 0.1 N, but higher and lower concentrations, around 0.05 N to 0.5 N, can be used without significant loss of SA values. For the hydrolysis, a temperature of 80° C. for one hour is preferred, but lower temperatures (e.g., 60° C.) for longer times or higher temperatures (up to reflux) for shorter times can also be used. The method of Warren (loc. cit.) is preferred for determining the sialic acid content, but other methods such as shown below and in the art, can also be employed.

As I have stated above, the resorcinol colorimetric test provides lower cancer/normal SA ratios than that of the TBA assay of Warren (vide supra). But the resorcinol method offers a rapid SA assay by being carried out in a homogeneous solution. As a comparison, however, the TBA test requires three extra steps: a cyclohexanone extraction of the red pigment from its water solution, a centrifugation, and a drying step.

Skoza et al., (Biochem. J., 159, 457-462, 1976) have found that with the help of dimethylsulfoxide in the TBA assay for SA determination, the red chromophore which was produced exhibited a molecular absorption coefficient of absorption of 68,000 at 549 nm. Ethyleneglycol and dimethylformamide provided similar molecular absorptions values.

I have now discovered that higher carbon atom containing, water miscible N,N-dialkylacylamides, more particularly N,N-dimethylacetamide, secured a homogeneous phase during the TBA determination of SA and resulted in a 28% higher molecular absorption coefficient: $\epsilon_{549}=87,000$, $\epsilon_{532}=35,000$ than that of Skoza's procedure. The red chromophore is stable for several hours. Under the same conditions, using N,N-dimethylacetamide as a cosolvent, the chromophore derived from the interfering deoxyribase showed an $\epsilon_{549}=61,000$ and $\epsilon_{532}=186,000$ values. N,N-diethylacetamide exhibited somewhat lower absorption maxima for SA at 549 nm (84,000) and at 532 nm (35,000).

In light of the well-known "garlic" odor and taste of the dimethylsulfoxide which penetrates through the skin, the practically odorless, higher carbon atom containing N,N-dialkylacylamides, such as N,N-dimethylacetamide, offer additional improvement in the determination of SA levels in biological fluids.

The following operating examples will more fully illustrate the method of my invention and its application to the detection of cancer.

EXAMPLE 1

Serum samples were obtained from 292 ostensibly healthy individuals; 113 cancer patients having no evidence of disease following treatment by surgery, radiation, and/or chemotherapy; 45 cancer patients in clinical remission; and 61 patients having active cancer. A wide range of primary sites were represented among these patients, including breast, colorectal, gynecological, head and neck, Hodgkin's disease, kidney, leukemia, liposarcoma, liver, lung, lymphoma, melanoma, myeloma, prostate, and stomach. All of the samples were evaluated by the following procedure:

A 0.5 ml serum sample was stirred for 10 minutes in an ice bath, 0.5 ml of aqueous 1.0 M p-toluenesulfonic acid (TSA) solution was added, and stirring was continued for 10 additional minutes in the ice bath. The resulting slurry was centrifuged 20 minutes at 3,000 rpm. A 0.5 ml aliquot of the supernatant was diluted with 2.0 ml of water at room temperature, then heated at 80° C. for 1 hour to cleave bound sialic acid from the glycoproteins. A 0.5 ml aliquot of the resulting hydrolysate was assayed for sialic acid content using Warren's thiobarbituric acid procedure. A Perkin-Elmer Model 124 double-beam grating spectrophotometer with a spectral bandwidth of 2 nm was used throughout this work. The measurements were made in 1 cm quartz cuvettes.

For the ostensibly healthy patients, the average sialic acid content was 85±16 mcg/ml. Accordingly, a cutoff point was determined at 118 mcg/ml (average plus two standard deviations), above which the existence of cancer was positively indicated.

The results of the TSA procedure were as follows:

| Patient Class | Number of Patients | Number of Samples | Average Sialic Acid Content ± S.D. | % True |
|---|---|---|---|---|
| Healthy | 292 | 292 | 85 ± 16 mcg/ml | 97 |
| Cancer, no evidence of disease | 113 | 165 | 96 ± 22 | 87[a] |
| Clinical Remission | 45 | 69 | 103 ± 33 | 77[b] |
| Active Cancer | 61 | 110 | 177 | 80 |

[a]One sample showed false positive at the time blood was drawn, but recurrence of active malignancy was observed two months later.
[b]Two samples showed false positive at the time blood was drawn, but recurrence of active malignancy was observed one and three months later.

EXAMPLE 2

Tests were run according to the method of Example 1, except after the acid hydrolysis of the supernatant, the hydrolysate was cooled to room temperature and a 0.5 ml aliquot was neutralized with 0.1 N sodium hydroxide. The neutralized aliquot was commingled with Aminoff's reagents (Skoza et al., loc. cit.), after which the red pigment was developed in a 100° C. water bath for eight minutes. The reaction mixture was then cooled in an ice bath and commingled with 2.5 ml N,N-dimethylacetamide, whereupon the brilliant red chromophore developed. The homogeneous, clear solution was read at $\lambda_{max}549$ and $\lambda_{max}532$ nm. The amount of sialic acid per milliliter of original serum was calculated using the following equation:

$$\text{mcg SA/ml serum} = [(A_{549} \times 0.060) - (A_{532} \times 0.020)] \times 309 \times 20$$

EXAMPLE 3

A further study was made on the sera of three healthy volunteers and three cancer patients to compare the basic amino acid content (arginine, histidine, and lysine) of the TSA and PCA supernatants. The results showed that the total quantity of basic amino acids in the TSA supernatants of the healthy volunteers was 23% higher than in the PCA supernatants; while it was only 13% higher in the cancer patients. Most strikingly, it was found that there was essentially no methionine or tyrosine in the PCA supernatants, while substantial amounts were present in the TSA supernatants, with marked elevation in the cancer patients:

|  | Methionine | Tyrosine |
|---|---|---|
| Healthy | | |
| TSA | 20.3 mcg/ml | 113.8 mcg/ml |
| PCA | 0 | 0 |
| Cancer | | |
| TSA | 37.6 mcg/ml | 234.8 mcg/ml |

| -continued | | |
|---|---|---|
| | Methionine | Tyrosine |
| PCA | 0 | trace |

While I have described my invention with reference to certain materials, techniques, and conditions, it is to be understood that such matters are included as illustrations only and not by way of limitation. Numerous modifications and equivalents will be apparent to those skilled in the art without departing from the spirit of the invention.

I claim:

1. A method for diagnosing and monitoring cancer in humans which comprises mixing benzenesulfonic acid, benzylsulfonic acid, a lower-alkylbenzenesulfonic acid or a lower-alkylbenzylsulfonic acid with human serum in an amount effective to precipitate components insoluble in the resulting acidic liquid phase without substantially affecting sialic acid level in the liquid phase, determining the sialic acid content of the acidic supernatant, and comparing said sialic acid content with the sialic acid content of healthy human sera after identical treatment.

2. A method for diagnosing and monitoring cancer in humans which comprises mixing a lower-alkylbenzenesulfonic acid with human serum in an amount effective to precipitate components insoluble in the resulting acidic liquid phase without substantially affecting sialic acid level in the liquid phase, determining the sialic acid content of the acidic supernatant, and comparing said sialic acid content with the sialic acid content of healthy human sera after identical treatment.

3. The method of claim 2 wherein said lower-alkylbenzenesulfonic acid is para-toluenesulfonic acid.

4. The method of claim 2 wherein the solids are separated from the acidic supernatant, and the acidic supernatant is diluted with water to around 0.1 N acid and heated to a temperature about 80° C. for a time sufficient to hydrolyze and release the covalently bound sialic acid contained therein.

5. The method of claim 2 wherein said lower-alkylbenzenesulfonic acid concentration in the supernatant is between about 0.1 M and about 1 M.

6. The method of claim 5 wherein said concentration is around 0.5 M.

7. The method of claim 5 wherein said human serum is commingled with 1.0 M acid and mixed in 1:1 ratio by volume.

8. The method of claim 4 wherein said sialic acid content of said healthy sera is about $85 \pm 16$ mcg/ml, and wherein the serum from a human having malignancy has a higher sialic acid content, measured after identical treatment.

9. A method of claim 8 wherein said sialic acid content of the supernatant is determined by thiobarbituric acid assay in aqueous N,N-dimethylacetamide.

10. A method for diagnosing and monitoring cancer in humans which comprises mixing aqueous 1.0 molar para-toluenesulfonic acid with an equal volume of human serum to precipitate components insoluble in said acid, separating the resulting solids, diluting the supernatant with water to 0.1 N acidity, heating the diluted supernatant at around 80° C. for about one hour, whereby sialic acid is released by hydrolysis from the glycoproteins contained therein, measuring the sialic acid thus released, and comparing the sialic acid thus obtained with the sialic acid obtained by identical treatment from a representative number of samples of serum from healthy humans.

* * * * *